United States Patent [19]

Mersch et al.

[11] Patent Number: 5,066,284
[45] Date of Patent: Nov. 19, 1991

[54] VENT FOR FLASHBACK PLUG

[75] Inventors: Steve H. Mersch, Germantown; David E. Spielvogel, Springboro; Charles W. Daugherty, Xenia, all of Ohio

[73] Assignee: Becton, Dickinson and Company, Franklin Lakes, N.J.

[21] Appl. No.: 350,960

[22] Filed: May 11, 1989

[51] Int. Cl.5 .............................................. A61M 5/178
[52] U.S. Cl. ..................................................... 604/168
[58] Field of Search ............... 604/168, 900, 129, 236, 604/238, 96; 606/194; 524/242

[56] References Cited

U.S. PATENT DOCUMENTS

| 4,193,399 | 3/1980 | Robinson | 128/214.4 |
| 4,200,096 | 4/1980 | Charvin | 604/168 |
| 4,269,186 | 5/1981 | Loveless et al. | 128/214.4 |
| 4,365,630 | 12/1982 | McFarlane | 128/214.4 |
| 4,481,314 | 11/1984 | Rule | 524/242 |
| 4,648,519 | 3/1987 | Kennedy | 215/261 |
| 4,682,980 | 7/1987 | Suzuki | 604/168 |
| 4,684,683 | 8/1987 | Ficker et al. | 524/242 |
| 4,767,408 | 8/1988 | McFarlane | 604/168 |
| 4,811,737 | 3/1989 | Rydell | 604/96 |
| 4,821,722 | 4/1989 | Miller et al. | 604/96 |
| 4,894,052 | 1/1990 | Crawford | 604/168 |
| 4,917,671 | 4/1990 | Chang | 604/168 |

Primary Examiner—C. Fred Rosenbaum
Assistant Examiner—Mark W. Bockelman
Attorney, Agent, or Firm—Robert P. Grindle

[57] ABSTRACT

A flashback vent plug is provided for catheters with air vents drilled by a laser beam which allow venting of the hollow plug upon venous entry, but which vents are so small that blood cannot pass. As a result, no leakage ever takes place. As a further feature of the invention, is the addition of a component to the resin making up the vent plug body which optimizes absorption of the laser beam wave length. The air vent design of this invention provides sufficient cross-section for achieving the required air flow, and therefore rapid flashback and venous entry indication, yet its cost of manufacture is considerably reduced when compared to plug designs that involve multi-step assembly.

14 Claims, 1 Drawing Sheet

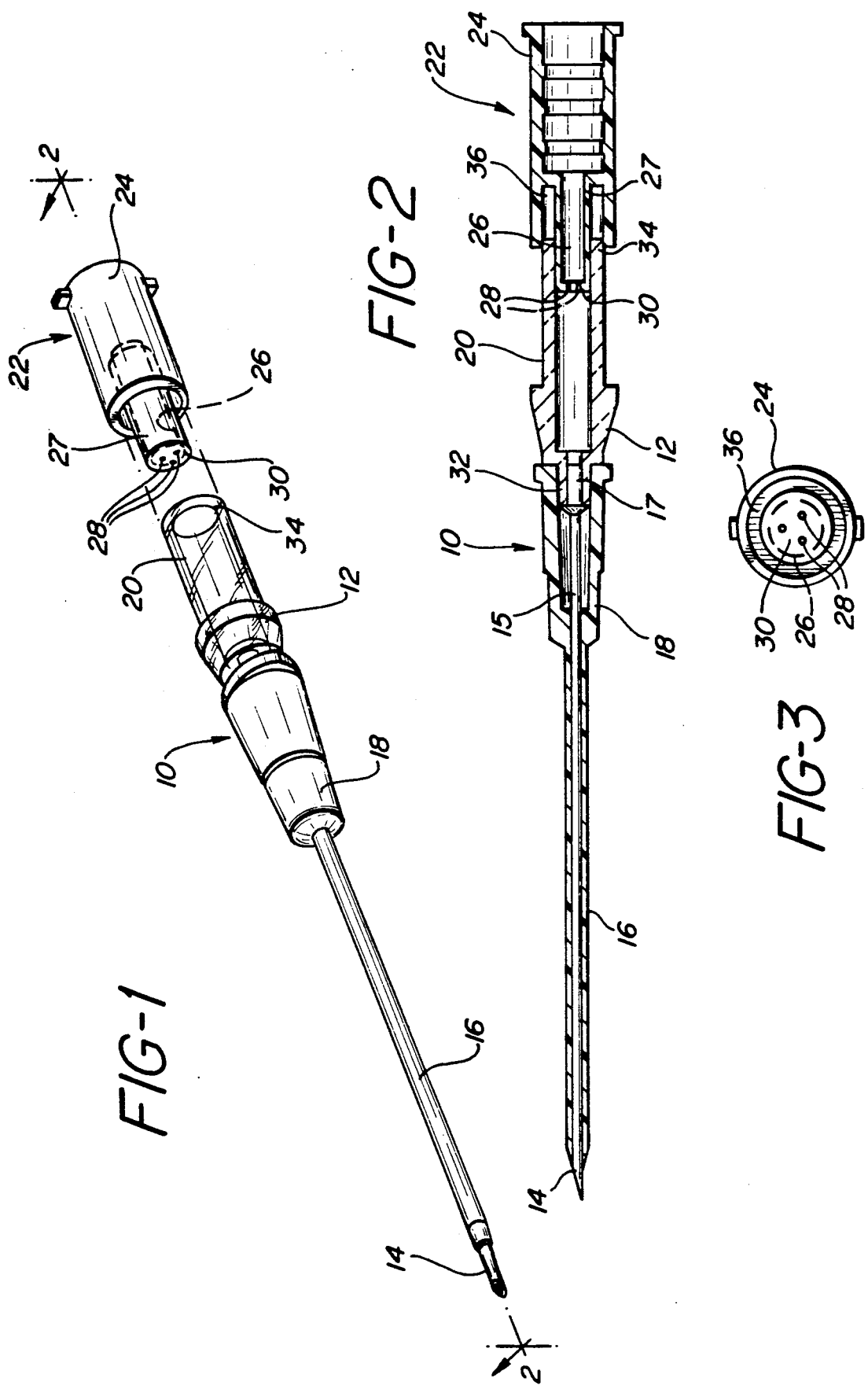

VENT FOR FLASHBACK PLUG

BACKGROUND AND STATEMENT OF THE INVENTION

This invention relates to intravenous needle assemblies and, more particularly, to a plug usuable with an intravenous needle for detecting the presence of the needle point within a blood vessel, and for preventing flow of blood from the assembly during the venous puncture procedure. The device provides for venting air rapidly, in order to enable the blood to flow from the blood vessel into a transparent blood-detecting chamber under venous pressure and in some cases more rapidly, than has been the case in the past, while at the same time preventing any blood flow through the vent passages.

During the placement of a needle or flexible catheter into a vein or other body member, it is desirable to determine whether or not the tip of the needle or catheter is properly situated within the vessel. Because the introduction of the assembly into the vein is normally accomplished by the use of an opaque rigid metallic needle, it is impossible to detect the presence of blood in the needle and needle hub.

Because of this, prior art introducer needles are equipped with a hub having a transparent flash chamber into which the blood flows to indicate that the needle point is properly placed. Many such devices, however, have leakage problems which cause blood flow over the hands of the user. It is important to avoid such circumstances, because of the potential for transfer of disease in exposure to blood from a patient. In providing a chamber with means for venting air therefrom so that the blood will flow rapidly into the chamber for indication of venous entry, the air vents have a tendency to leak.

With this invention, by contrast, a flashback assembly is provided with transparent walls to indicate the presence of blood in the hub of the assembly and that the needle has, indeed, entered the vein of a patient, with the vent being comprised of a required cross section of actual venting area, but with vent holes much smaller than those achieved in the prior art. This is arranged in accordance with this invention by the use of a laser for drilling the vent holes. By doing so, the laser provides the same or a greater cross sectional area of actual air venting, while at the same time providing holes which are small enough to prevent the leakage of blood through the air vents.

In accordance with this invention, a laser is used for drilling one or an array of small holes in the end of the flow control plug. The hole or holes comprise a total sufficient cross sectional area to provide flashback times at least equivalent or better than the prior art plugs utilizing other conventional venting methods such as membranes, sintered thermoplastics, or slit valves.

The laser utilized for drilling the holes may be, for example, a YAG laser (yttrium-aluminum-garnet). Also, a ruby laser may be utilized, but the YAG laser is preferred. The holes will have a diameter of less than 0.002 inches and, preferably, less than 0.001 inch. In this connection, it has been determined that holes of 0.003 inches or above in diameter leak blood at venous pressures.

In considering generally the conditions for carrying out the invention herein, it has been determined that conventional thermoplastic materials such as polyethylene do not absorb the laser beam wave length to the level required for producing the holes in accordance herewith, without containing an additive which increases absorption. Thus, it was found in accordance with this invention that an additive such as ACRA WAX ® added to the material under consideration provides the proper absorption characteristics for plugs made in accordance with this invention. That is, it is important that when the holes are being drilled a proper level or degree of absorption of a laser wave length takes place in order to achieve vaporization of the material, and, hence, properly drilled holes. If the proper level is not obtained, melting of the material takes place with clogging of such small holes.

Thus, pellets of polyethylene were provided with a one percent quantity, by weight, of ACRA WAX ® and extruded into ribbons of about 0.005 inches thick. Circular samples of this material were drilled with the YAG laser. A sample with three holes drilled in the sample with each hole of less than 0.002 inches in diameter were tested utilizing a dyed water to indicate the presence of the liquid in the plug of the invention. The test indicated not only rapid flashback time but an absence of leakage.

In considering further the conditions for carrying out the invention here, the following thermoplastic materials are representative of materials which may be utilized for formulating the plugs of the invention. These materials are polyethylene as indicated above, polypropylene, polyvinyl chloride, acrylonitrile butadiene-styrene terpolymer, polyethylene terephthalate and poly urethane. It will be understood that other materials may be used as long as they come within the operating parameters discussed herein. While most materials listed above will not have the appropriate absorption requirement necessary for laser drilling as discussed herein, it should be understood that some materials will, indeed, have those characteristics, thus eliminating the need for an additive for that purpose.

Examples of additives which may be used to increase the absorption properties of the thermo plastics utilized with the invention here include ADVAWAX 280 ®, a product of Morton Thiokol, or ACRA WAX ® C lubricant, a product of Glyco Incorporated, 488 Main Street, P.0. Box 5100 Norwalk, Conn. 06856. ACRA WAX is an alkyl amide which is the reaction product of ethylene diamine and stearic acid. The specific name is N,N'-ethylene bis(stearamide). The additive may be mixed with the resin at the rate of within the range of between about 0.5 and 5 percent by weight, and, preferably, within the range of between about 1.0 and 3.0 percent by weight.

In order to prepare the plugs of the invention, the following example indicates one representative procedure for making such plugs.

EXAMPLE

Polyethylene pellets (Eastman 1870A) were melt processed and mixed with 1.0 percent ACRA WAX ®, using a twin screw extruder/pelletizer. After drying, the pellets were molded into the desired plug shape. The appropriate size and number of holes were then drilled using a YAG laser as discussed above. In this connection the wall of the plug to be drilled was arranged to have in the area where the holes are to be drilled an even unvarying width of about 0.005 inches in thickness. Subsequently, the holes, as discussed above, were drilled by the laser in this wall portion.

Other objects and advantages of this invention will be apparent from the following description, the accompanying drawings and the appended claims.

DESCRIPTION OF THE DRAWINGS

FIG. 1 is an exploded perspective view of an intravenous needle assembly showing the plug of the present invention in a position removed from the end of the blood detecting chamber;

FIG. 2 is a longitudinal cross-sectional view of the needle assembly of FIG. 1 showing the plug of the invention inserted within the blood-detecting chamber; and FIG. 3 is an end view of the plug as viewed from the left in FIG. 2.

Referring to the drawings in which like reference characters refer to like parts throughout the several views thereof, FIGS. 1 and 2 illustrate the vent plug of the invention as used in an intravenous needle assembly as shown generally at 10. The assembly includes an introducer needle 15 which is in the form of a hollow hypodermic needle having a point 14 on one end thereof. Needle 15 is secured at its blunt end to a plastic hub 12 which has a transparent blood detecting chamber 20 integral with its proximal end. The entire hub and blood detecting chamber assembly may, preferably, be molded in one piece from a suitable clear plastic material.

In the preferred embodiment, needle 15 serves the function of introducing a flexible plastic catheter 16 into a vein or other body vessel. Catheter 16 is attached to a hub 18 at its proximal end, and hub 18 is adapted to be removably secured to a fitting 32 on the distal end of hub 12.

The present invention eliminates the necessity for any complex form of operation necessary to indicate venous entry and provides a relatively simple, one piece plug which performs the function of rapid indication of venous entry. This is achieved with the plug of the invention by having an increased cross sectional vent area combined for venting air from the plug, so that when venous entry is made the blood flows rapidly into and fills up the transparent chamber in the hub of the assembly, as discussed herein. Nevertheless, the individual holes are of such small dimension that blood will not flow through them so that there is no contamination to the user of the device by the blood of a patient upon which the assembly of the invention is being utilized. This reduces the exposure to AIDS, hepatitis or other diseases carried by the blood of patients, for example.

The plug of the invention is shown generally in FIG. 1 at 22 and includes a substantially cylindrical body portion 24 having extending from the front end thereof, a neck portion 27. As can be seen in FIG. 2, neck portion 27 includes an internal cylindrical passage 26. The front face 30 of neck portion 27 is a wall of substantially even thickness, as discussed above. The wall 30 is formed so that it has a thickness of around 0.005 inches in order to be appropriate for receiving a plurality of laser drilled openings 28. As discussed above, laser openings 28 are drilled to have a diameter of less than 0.002 inches and preferably 0.001 inch.

The number of laser drilled holes 28 provided will depend upon the dimension of the assembly being utilized and the volume of air required to be vented through holes 28 from the transparent chamber 20, so that when the point 14 of needle 15 is inserted into the vein of a patient blood will flow rapidly back through needle 15 into the transparent chamber 20. This happens because the air under venous pressure moves rapidly through vent holes 28. As can be seen in FIG. 3, three such vent holes 28 are shown. However, a greater number may be selected, as discussed above, depending upon the desired properties for the individual plug being formulated.

To initiate the introduction of a needle into a vein, in accordance with the unit of the invention herein, the unit is fully assembled as shown in FIG. 2 with catheter 16 positioned over needle 15 and with plug 22 firmly seated into the rear or proximal end of blood detecting chamber 20. The introduction of the needle point 14 into a vein causes blood to flow through the hollow needle and into the blood detecting chamber 20.

Air contained within the hollow needle and the blood detecting chamber will be forced by the blood through the vent holes 28 out into the atmosphere. Obviously, blood flowing into chamber 20 will be detected by the operator through the transparent wall thereof. Because of the extremely small size of the vent holes 28, blood will be retained within the chamber and not permitted to pass to the passage 26 in plug 22. Thereafter, when it is desired to attach an administration set or other device to the catheter hub, it is only necessary to withdraw the needle from the catheter and, thereby, expose the open female luer end of hub 18 for the appropriate male fitting.

Alternatively, needle 15 may be used independently of catheter 16 and an administration set or other device may be attached directly to the blood detecting chamber 20 by merely removing plug 22 therefrom.

As will be apparent from the foregoing, the invention herein provides an effective device for detecting the presence of an introducer needle point within the vein of a patient and for preventing the loss of blood from the needle assembly. Moreover, the device of the invention may be made with relatively inexpensive materials and known conventional equipment which makes the plug of the invention particularly appropriate for mass production techniques and reduced cost.

While the form of apparatus herein described constitutes a preferred embodiment of the invention, it is to be understood that the invention is not limited to the precise form of apparatus shown, and that changes may be made therein without departing from the scope of the invention which is defined in the appended claims. For example, as discussed previously, a greater or lesser number of holes may be drilled by the laser beam with the limitation only being the requirement for the particular plug dimensions being utilized. More over, a wide variety or selection of thermoplastic materials may be utilized provided the appropriate additive is selected, when required, in the proper quantity in order to increase absorption of the laser beam wave length appropriately to the level required for vaporization of the material being worked upon as opposed to melting that material. That is, in order to provide effective holes of such small dimension, it is necessary for the material to be vaporized. If the material melts then the proper holes will not be provided in such small dimensions.

Alternatively, as will be understood by practitioners in the art materials may be selected which have sufficient absorption characteristics so that an additive is not required.

What is claimed is:

1. A plug for use in plugging the proximal end of a transparent flashback chamber in an intravenous needle assembly, said plug for providing air venting of said flashback chamber, said plug comprising
(a) an integral one-piece molded hollow body defining an air vent passage;
(b) a hollow neck portion positioned on the distal end of said body, said neck portion being integral with said body portion;
(c) a front face on the distal end of said neck portion;
(d) said front face being thin-walled and of the same thickness throughout;
(e) a plurality of vent holes in said front face;
(f) said vent holes being laser drilled vent holes;
(g) at least said thin-walled front face being comprised of a thermoplastic material having sufficient laser absorption characteristics to vaporize under the effect of a laser beam; and
(h) said thin-walled front face having in percent be weight an amount of an additive effective for optimizing said vaporization.

2. The plug of claim 1, further characterized by
(a) said plug being comprised of a material selected from the group consisting of polyethylene, polypropylene, polyvinyl chloride, acrylonitrile-butadiene-styrene terpolymer, polyethylene terephthalate, polyurethane and mixtures thereof.

3. The plug of claim 1, further characterized by
(a) said front face having a thickness of about 0.005 inches.

4. The plug of claim 1, further characterized by
(a) said plurality of vent holes having a diameter within the range of between about less than 0.001 inch and 0.002 inches.

5. The plug of claim 1, further characterized by
(a) said additive is present in percent by weight within the range of between about 0.5 and 5 percent.

6. The plug of claim 1, further characterized by
(a) said additive is a reaction product of ethylene diamine and stearic acid.

7. The plug of claim 6, further characterized by
(a) said additive is N,N'-ethylene bis(stearamide).

8. An intravenous needle assembly comprising
(a) a hollow pointed needle;
(b) a hub secured to the proximal end of said needle;
(c) said hub having a transparent blood detecting chamber;
(d) a plug removably secured in said chamber;
(e) said plug for venting air from said transparent blood-detecting chamber;
(f) said plug consisting of
  (1) an integral one-piece molded hollow body defining an air vent passage;
  (2) a hollow neck portion positioned on the distal end of said body, said neck portion being integral with said body portion;
  (3) a front face on the distal end of said neck portion;
  (4) said front face being thin-walled and of the same thickness throughout;
  (5) a plurality of vent holes in said front face;
  (6) said vent holes being laser drilled vent holes;
  (7) at least said thin-walled front face being comprised of a thermoplastic material having sufficient laser absorption characteristics to vaporize under the effect of a laser beam; and
  (8) said thin-walled front face having in percent by weight an amount of an additive effective for optimizing said vaporization.

9. The needle assembly of claim 8, further characterized by
(a) said plug being comprised of a material selected from the group consisting of polyethylene, polypropylene, polyvinyl chloride, acrylonitrile-butadiene-styrene terpolymer, polyethylene terephthalate, polyurethane, and mixtures thereof.

10. The needle assembly of claim 8, further characterized by
(a) said front face having a thickness of about 0.005 inches.

11. The needle assembly of claim 8, further characterized by
(a) said plurality of vent holes having a diameter within the range of between about less than 0.001 inch and 0.002 inches.

12. The needle assembly of claim 8, further characterized by
(a) said additive is present in percent by weight within the range of between about 0.5 and 5 percent.

13. The needle assembly of claim 8, further characterized by
(a) said additive is a reaction product of ethylene diamine and stearic acid.

14. The needle assembly of claim 12, further characterized by
(a) said additive is N,N'-ethylene(bis stearamide).

* * * * *